US012790573B2

(12) United States Patent
Lucas

(10) Patent No.: US 12,790,573 B2
(45) **Date of Patent: *Nov. 10, 2026**

(54) ETHANOL PRODUCTION SYSTEM AND METHOD

(71) Applicant: LucasE3, L.C., Shawnee, KS (US)

(72) Inventor: Scott A. Lucas, De Soto, KS (US)

(73) Assignee: LucasE3, L.C., Lenexa, KS (US)

( * ) Notice: Subject to any disclaimer, the term of this patent is extended or adjusted under 35 U.S.C. 154(b) by 1126 days.

This patent is subject to a terminal disclaimer.

(21) Appl. No.: 17/830,623

(22) Filed: Jun. 2, 2022

(65) Prior Publication Data

US 2023/0138705 A1 May 4, 2023

Related U.S. Application Data

(60) Provisional application No. 63/273,014, filed on Oct. 28, 2021.

(51) Int. Cl.

| | |
|---|---|
| ***C12M 1/00*** | (2006.01) |
| ***C10L 1/02*** | (2006.01) |
| ***C12M 1/34*** | (2006.01) |
| ***C12P 7/06*** | (2006.01) |

(52) U.S. Cl.

CPC ............... *C12M 21/12* (2013.01); *C10L 1/02* (2013.01); *C12M 23/40* (2013.01); *C12M 29/04* (2013.01); *C12M 41/12* (2013.01); *C12P 7/06* (2013.01); *C10L 2200/0469* (2013.01)

(58) Field of Classification Search

None

See application file for complete search history.

(56) References Cited

U.S. PATENT DOCUMENTS

| | | | | |
|---|---|---|---|---|
| 2,958,142 | A | | 11/1960 | Kershaw et al. |
| 3,363,340 | A | | 1/1968 | Mckinley |
| 3,673,705 | A | | 7/1972 | Wright et al. |
| 4,309,254 | A | | 1/1982 | Dahlstrom |
| 5,178,543 | A | | 1/1993 | Semans et al. |
| 5,354,203 | A | | 10/1994 | Kotch et al. |
| 7,504,546 | B2 | | 3/2009 | Brown et al. |
| 7,867,365 | B2 | | 1/2011 | Brown |
| 7,988,580 | B2 | | 8/2011 | McCrary |
| 8,123,864 | B2 | * | 2/2012 | Christensen ........... C12M 45/09 44/605 |
| 8,173,412 | B2 | | 5/2012 | Dale |
| 9,029,126 | B2 | | 5/2015 | Bleyer et al. |
| 9,308,489 | B2 | | 4/2016 | Brown et al. |
| 9,931,582 | B2 | | 4/2018 | Furlong |
| 10,315,127 | B2 | | 6/2019 | Mösslein et al. |
| 10,683,479 | B2 | * | 6/2020 | Lucas .................... C12M 47/08 |
| 11,186,851 | B2 | * | 11/2021 | Lucas ........................ C12P 7/08 |
| 11,268,062 | B2 | * | 3/2022 | Lucas ................ B01D 11/0446 |
| 12,006,377 | B2 | * | 6/2024 | Lucas .................... B01D 35/26 |
| 2009/0171724 | A1 | | 7/2009 | Allin et al. |
| 2011/0315541 | A1 | | 12/2011 | Xu |
| 2012/0211411 | A1 | * | 8/2012 | Hopkins ............ B01D 39/1623 210/333.01 |
| 2014/0053829 | A1 | | 2/2014 | Lee |
| 2014/0343259 | A1 | | 11/2014 | Bleyer et al. |
| 2015/0041305 | A1 | | 2/2015 | Overheul et al. |
| 2015/0045594 | A1 | | 2/2015 | Overheul et al. |
| 2015/0238881 | A1 | | 8/2015 | Bleyer et al. |
| 2016/0024406 | A1 | * | 1/2016 | Javers .................... B01D 3/005 435/162 |
| 2016/0279560 | A1 | | 9/2016 | Furlong |
| 2018/0290073 | A1 | | 10/2018 | Brown et al. |
| 2019/0076751 | A1 | | 3/2019 | Lucas |
| 2019/0233354 | A1 | | 8/2019 | Lucas |
| 2019/0336882 | A1 | | 11/2019 | Andrade et al. |
| 2020/0171404 | A1 | | 6/2020 | Lucas |

FOREIGN PATENT DOCUMENTS

| | | | | |
|---|---|---|---|---|
| AU | 2007303117 | | 4/2008 | |
| WO | WO-2012131700 A2 | * | 10/2012 | .............. C12P 19/14 |

OTHER PUBLICATIONS

Katzen , et al., "Ethanol Distillation: the Fundamentals", 1999, 270-273.

Raab, Michael , "Enahnced for Ethanol", Ethanol Producer Magazine, Oct. 2019, ethanolproducer.com/articles/16511/enhanced-for-ethanol, Sep. 16, 2019, 1-2.

* cited by examiner

*Primary Examiner* — Christian L Fronda

(74) *Attorney, Agent, or Firm* — Erise IP, P.A.

(57) ABSTRACT

A system and method for producing ethanol from dry-milled corn or other grains includes the steps of separating fiber components and embedded starch components from the grain. The fiber components and embedded starch components are cooked at high temperatures and fermented to produce ethanol.

17 Claims, 1 Drawing Sheet

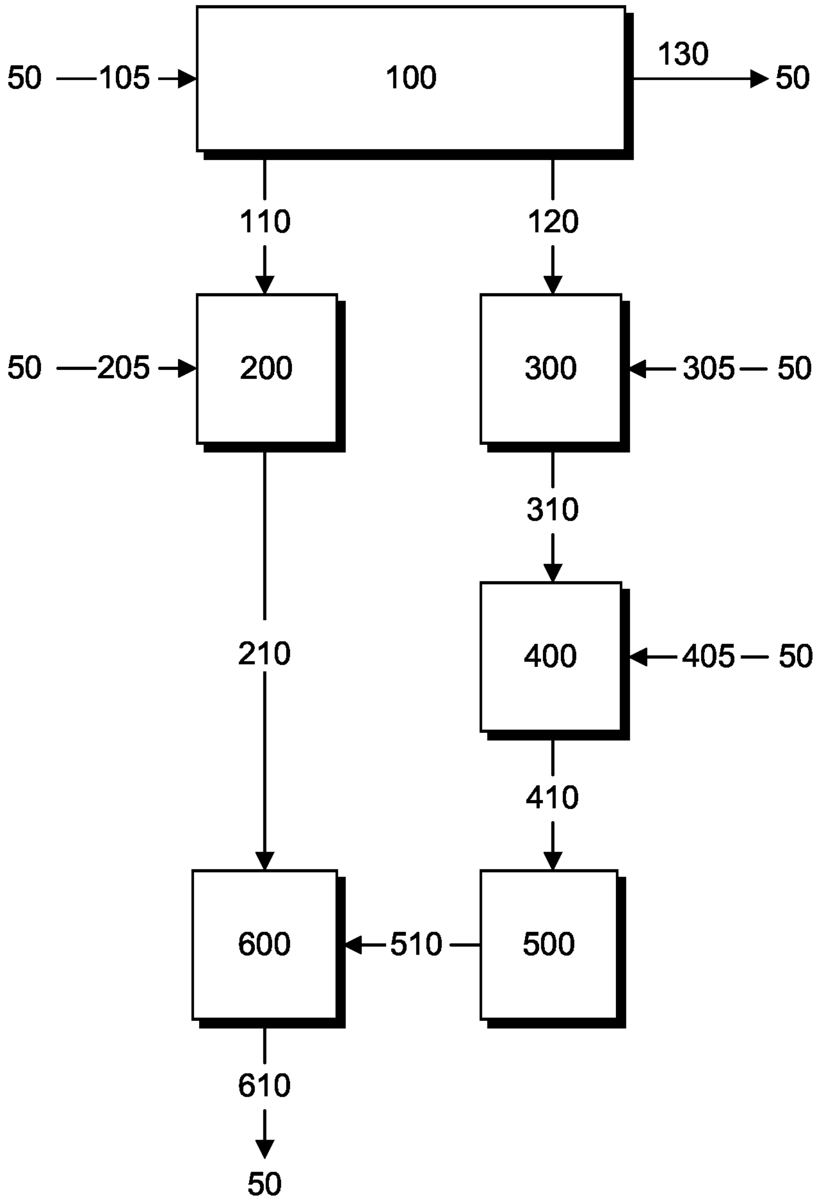
50
105
100
130
50
110
120
50
205
200
300
305
50
310
400
405
50
210
410
600
510
500
610
50

ETHANOL PRODUCTION SYSTEM AND METHOD

CROSS-REFERENCE TO RELATED APPLICATION

This application is a continuation-in-part of and claims priority in U.S. Patent Application No. 63/273,014 filed Oct. 28, 2021 which is incorporated herein by reference.

BACKGROUND OF THE INVENTION

1. Field of the Invention

Dry milling of corn and other grains is used to prepare feedstock for producing ethanol through fermentation of the starch components in the feedstock grain. The ethanol product output is used in fuel and other applications.

Corn and other grains contain components other than starch, such as fiber, sugars, oil, ash and protein. The fiber components typically contain embedded starch components, which is unavailable for ethanol production and passes through the plant unconverted.

2. Description of the Related Art

Various methods are available for processing the fiber components of feedstock grain in such a way as to make the resulting starch available for ethanol production. However, heretofore there has not been available an alternative corn cooking system with the advantages and features of the present invention.

BRIEF SUMMARY OF THE INVENTION

The proposed method is a unique method for efficiently processing the fiber component to increase the starch conversion of ground corn. Use of high temperature to cook ground corn or starch containing materials is known in the art. The method of separating out the fiber components first, to reduce the total amount of material that must be heated to high temperature, improves the concept by reducing the amount of steam needed to achieve the same results.

The fiber components are separated from the other components in the ground corn by use of a flour screening device. The ground corn is diverted to the flour screening device to separate the ground corn into two streams. A fine particulate flour which will contain most of the starch will pass through the screen and be sent back to the ethanol plant untreated. The larger particle fiber components will be diverted to the new process where the material will be exposed to very high temperature conditions, above 250° F., to allow the embedded starch components in the fiber to be removed from fiber and made available for fermentation to ethanol. The treated fiber components are sent back to the ethanol plant and blended back with the starch containing flour stream.

By separating the fiber components out of the ground corn first, the high temperature process used will be more efficient as less steam will be required for this system as only 50% of the ground corn components will need to be treated. This will keep the steam usage minimized.

BRIEF DESCRIPTION OF THE DRAWINGS

The drawings constitute a part of this specification and include exemplary embodiments of the present invention and illustrate various objects and features thereof.

FIG. 1 is a schematic diagram of a system for producing ethanol from grain embodying an aspect of the present invention.

DETAILED DESCRIPTION OF THE PREFERRED EMBODIMENT

I. Introduction and Environment

As required, detailed aspects of the present invention are disclosed herein; however, it is to be understood that the disclosed aspects are merely exemplary of the invention, which may be embodied in various forms. Therefore, specific structural and functional details disclosed herein are not to be interpreted as limiting, but merely as a basis for the claims and as a representative basis for teaching one skilled in the art how to variously employ the present invention in virtually any appropriately detailed structure.

Certain terminology will be used in the following description for convenience in reference only and will not be limiting. The words, “inwardly” and “outwardly” refer to directions toward and away from, respectively, the geometric center of the aspect being described and designated parts thereof. Said terminology will include the words specifically mentioned, derivatives thereof and words of similar meaning.

II. Preferred Embodiment Ethanol Production System and Method

Ground corn 105, diverted from an existing plant 50, is fed to a flour screen 100 with sufficient screens to allow for separation of the ground corn 105 into three separate components. Unground corn 130, will be removed and sent back to the plant 50. Fine particulate flour 110 will pass through the screens and is fed to a flour mix tank 200. Process water 205 from the existing plant 50 is mixed with the flour to produce a flour slurry, 210, at about 30% wt solids. The flour slurry 210 is pumped to the slurry mixer 600.

Larger particulate fiber components, which are shown at 120, are separated by the flour screen 100 and diverted to a fiber mix tank 300. Process water 305, from the existing plant 50, is mixed with the fiber components 120 to produce a fiber slurry 310 at about 30% wt solids. The fiber slurry 310, is pumped and fed to a high temperature jet cooker 400, where high pressure steam 405, from the existing plant 50, is mixed with the fiber slurry 310, to produce a high temperature slurry 410 at above 250° F.

The high temperature slurry 410 is fed to a high temperature cook tube 500, where the mixture will be kept at above 250° F. for approximately 10 minutes. After being held in the high temperature cook tube 500, the cooked fiber 510 will be fed to the slurry mixer 600 where the cooked fiber 510 is blended with the flour slurry 210 to produce a stream of warm slurry 610 at approximately 185° F., which is sent to the existing ethanol plant 50.

It is to be understood that while certain embodiments and/or aspects of the invention have been shown and described, the invention is not limited thereto and encompasses various other embodiments and aspects.

Having thus described the invention, what is claimed as new and desired to be secured by Letters Patent is:

1. A system for producing ethanol from grain in an ethanol plant, comprising:

a flour screen configured for receiving ground grain from the ethanol plant and separating fiber components of the grain from other components; and a cooking system comprising a jet cooker configured to receive steam from the ethanol plant and a high temperature cook tube configured to receive a slurry, the slurry comprising the fiber components, from the jet cooker and maintain said slurry at a temperature above 220° F. for 5 to 15 minutes to release embedded starch components for fermentation to ethanol.

2. The system according to claim 1, further comprising:

a flour mix tank configured for receiving fine particulate flour separated by the flour screen and mixing said fine particulate flour with process water from the ethanol plant to produce a flour slurry.

3. The system according to claim 2, wherein the flour screen separates the ground grain into:

unground corn for removal and return to the plant; fine particulate flour configured for passing through the flour screen, and feeding to a flour mix tank;

fine particulate flour configured for passing through the flour screen, and feeding to a flour mix tank; and process water from the ethanol plant mixed with flour to produce the flour slurry, which is pumped to a slurry mixer.

4. The system according to claim 3, further comprising:

a fiber mix tank configured for receiving particulate fiber components separated by the flour screen and mixing said fiber components with process water from the ethanol plant to produce a fiber slurry.

5. The system according to claim 4, wherein the ethanol plant includes a source of process water.

6. The system according to claim 5, wherein said process water is mixed with said fiber components to produce a fiber slurry.

7. The system according to claim 6, wherein said fiber slurry is at about 20%-40% wt solids.

8. The system according to claim 7, further comprising:

a jet cooker;

said jet cooker is configured to receive steam from the ethanol plant; and said jet cooker is configured for mixing fiber slurry.

9. The system according to claim 8 wherein said slurry is heated to a temperature greater than 220° F.

10. The system according to claim 9, further comprising:

a high temperature cook tube configured to receive the slurry.

11. The system according to claim 10 wherein said slurry in said cook tube is maintained at a temperature above 220° F. for 5 to 15 minutes.

12. The system according to claim 11, further comprising:

a slurry mixer configured for receiving cooked fiber from said cook tube; and said slurry mixer is configured for blending said cooked fiber and said flour slurry to produce a stream of warm slurry.

13. The system according to claim 12 wherein:

said slurry mixer is configured to maintain said stream of warm slurry at a temperature in the range of 160° F. to 210° F.; and said slurry mixer is configured to send said stream of warm slurry to the plant.

14. A system for producing ethanol from grain in an ethanol plant, comprising:

a flour screed connected to the ethanol plant and configured for separating fiber components of the grain from other components;

a cooking system connected to the flour screen and comprising a jet cooker configured to receive steam from the ethanol plant and a high temperature cook tube configured to receive slurry from the jet cooker and maintain the slurry at a temperature above 220° F.;

a flour screen connected to said cooking device and configured for: receiving ground grain from the ethanol plant; separating said ground grain into multiple components for processing, including: unground corn for removal and return to the plant; fine particulate flour configured for passing through the flour screen and feeding to a flour mix tank; fine particulate flour configured for passing through the flour screen and feeding to a flour mix tank;

a slurry mixer configured for receiving process water from the existing plant and mixing said process water with flour to produce a flour slurry;

a fiber mix tank configured for receiving said flour slurry and diverting particulate fiber components separated by the flour screen to said fiber mix tank;

a jet cooker configured to receive steam from said plant;

said jet cooker is configured for mixing fiber slurry; and a high temperature cook tube configured to receive the slurry.

15. The system according to claim 14 wherein said slurry in said cook to is maintained at a temperature above 220° F. for 5 to 15 minutes.

16. The system according to claim 15, comprising:

a slurry mixer configured for receiving cooked fiber from said cook tube; and said slurry mixer is configured for maintaining the stream of warm slurry at a temperature in the range of 160° F. to 210° F. and sends the warm slurry to the ethanol plant.

17. The system according to claim 14 wherein said slurry mixer is configured to blend the cooked fiber and the flour slurry to produce the stream of warm slurry prior to fermentation in the ethanol plant.

* * * * *